US010072245B2

(12) United States Patent
Bosio et al.

(10) Patent No.: US 10,072,245 B2
(45) Date of Patent: Sep. 11, 2018

(54) METHOD FOR GENERATION OF A CELL COMPOSITION OF MESENCEPHALIC DOPAMINERGIC PROGENITOR CELLS

(71) Applicant: Miltenyi Biotec GmbH, Bergisch Gladbach (DE)

(72) Inventors: Andreas Bosio, Cologne (DE); Sebastian Knobel, Cologne (DE); Daniela Lehnen, Cologne (DE); Serena Barral, London (GB)

(73) Assignee: Miltenyi Biotec GmbH, Bergisch-Gladbach (DE)

( * ) Notice: Subject to any disclaimer, the term of this patent is extended or adjusted under 35 U.S.C. 154(b) by 5 days.

(21) Appl. No.: 15/055,414

(22) Filed: Feb. 26, 2016

(65) Prior Publication Data
US 2017/0247657 A1 Aug. 31, 2017

(30) Foreign Application Priority Data

Feb. 27, 2015 (EP) .................................... 15157057

(51) Int. Cl.
*C12N 5/0797* (2010.01)
*A61K 35/30* (2015.01)
(52) U.S. Cl.
CPC ............ *C12N 5/0623* (2013.01); *A61K 35/30* (2013.01); *C12N 2501/599* (2013.01); *C12N 2506/03* (2013.01)
(58) Field of Classification Search
None
See application file for complete search history.

(56) References Cited

U.S. PATENT DOCUMENTS

| 2005/0196864 | A1* | 9/2005 | Goldman | C12N 5/0623 |
| | | | | 435/456 |
| 2010/0021437 | A1* | 1/2010 | Isacson | C12N 5/0618 |
| | | | | 424/93.7 |
| 2013/0021437 | A1 | 1/2013 | Liu | |

FOREIGN PATENT DOCUMENTS

| WO | WO-2009/072003 A2 | 6/2009 |
| WO | WO-2009/072003 A3 | 6/2009 |
| WO | WO-2011/041062 A1 | 4/2011 |
| WO | WO-2013/015457 A1 | 1/2013 |
| WO | WO-2013/067362 A1 | 5/2013 |
| WO | WO-2013/155109 A1 | 10/2013 |

OTHER PUBLICATIONS

Barker, R.A. et al. (Jan. 2013). "Fetal Dopaminergic Transplation Trials and the Future of Neural Grafting in Parkinson's Disease," *Lancet Neurol.* 12(1):84-91.

Doi, D. et al.(Mar. 11, 2014). "Isolation of Human Induced Pluripotent Stem Cell-Derived Dopaminergic Progentiros by Cell Sorting for Successful Transplantation," *Stem Cell Reports ISSCR* 2(3):337-350.
Dos Santos, F.F. et al. (2013). "Bioreactor Design for Clinical-Grade Expansion of Stem Cells," *Biotechnol. J.* 8(6):644-654.
Drui, G. et al. (2013, e-pub. Feb. 12, 2013). "Loss of Dopaminergic Nigrostriatal Neurons Accounts for the Motivational and Affective Deficits in Parkinson's Disease," *Molecular Psychiatry* 19(3):358-367, (pp. 1-10).
Grealish, S. et al. (Nov. 6, 2014). "Human ESC-Derived Dopamine Neurons Show Similar Preclinical Efficacy and Potency to Fetal Neurons When Grafted in a Rat Model of Parkinson's Disease," *Cell Stem Cell* 15(5):653-665.
Huang, X. et al. (2004, e-pub. Aug. 26, 2004). "Induction of the Neural Crest and the Opportunities of Life on the Edge," *Development Biology* 275:1-11.
Kefalopoulou, Z. et al. (Jan. 2014, e-pub. Nov. 18, 2014). "Long-Term Clinical Outcome of Fetal Cell Transplantation for Parkinson Disease Two Case Reports," *JAMA Neurol.* 71(1):83-87.
Kirkeby, A. et al. (Jun. 28, 2012). "Generation of Regionally Specified Neural Progenitors and Functional Neurons from Human Embryonic Stem Cells Under Defined Conditions," *Cell Reports* 1(6):703-714.
Kriks, S. et al. (Dec. 2011). "Dopamine Neurons Derived From Human ES Cells Efficiently Engraft in Animal Models of Parkinson's Disease," *Nature* 480(7378):547-551.
Otsuji, T.G. et al. (May 6, 2014). "A 3D Sphere Culture System Containing Functional Polymers for Large-Scale Human Pluripotent Stem Cell Production," *Stem Cell Reports ISSCR* 2(5):734-745.
European Search Report and Search Opinion dated Jul. 21, 2015, for EP Application No. 15157056.9, filed on Feb. 27, 2015, 8 pages.
Lehnen, D. et al. (Oct. 10, 2017). "IAP-Based Cell Sorting Results in Homogeneous Transplantable Dopaminergic Precursor Cells Derived from Human Pluripotent Stem Cells," with Supplmental Information *Stem Cell Reports* 9:1-14. (Total pp. 26).

* cited by examiner

*Primary Examiner* — Renee Claytor
*Assistant Examiner* — Susan E. Fernandez
(74) *Attorney, Agent, or Firm* — Morrison & Foerster LLP

(57) ABSTRACT

The present invention provides a method for generation of a cell composition of mesencephalic dopaminergic progenitor cells from a starting cell composition comprising pluripotent and/or multipotent stem cells, the method comprising the steps of a) differentiating said pluripotent and/or multipotent stem cells into mesencephalic dopaminergic progenitor cells, thereby generating a cell population comprising mesencephalic dopaminergic progenitor cells and other cells, b) dissociating the differentiated cells of step a) into a single cell suspension, and c) enriching said mesencephalic dopaminergic progenitor cells by using an antigen binding molecule specific for the CD47 antigen for positive selection of said mesencephalic dopaminergic progenitor cells in said single cell suspension. Said method may be performed in a closed cell sample processing system and may be performed in an automated manner.

7 Claims, 7 Drawing Sheets

LMX1A

FOXA2

FIG. 6
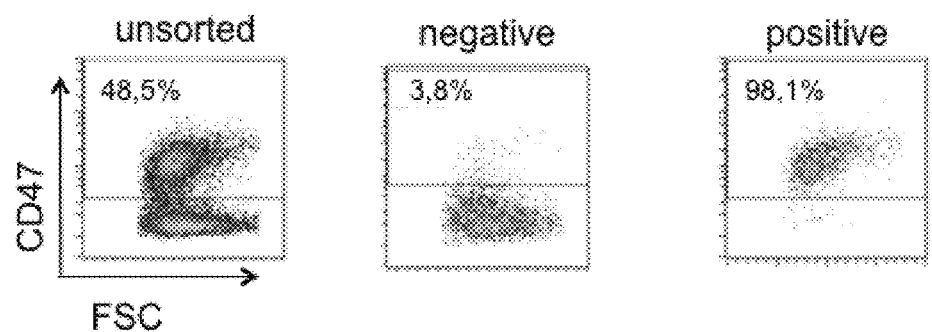
FIG. 7A  Unsorted cells
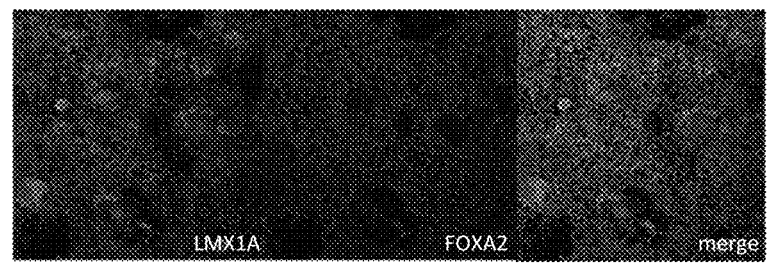
FIG. 7B  Positive Fraction
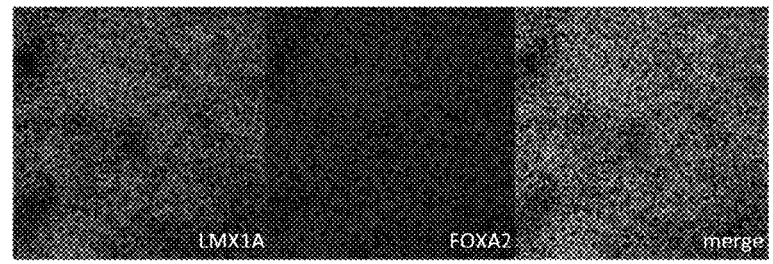

METHOD FOR GENERATION OF A CELL COMPOSITION OF MESENCEPHALIC DOPAMINERGIC PROGENITOR CELLS

CROSS REFERENCE TO RELATED APPLICATIONS

This application claims priority to European Application No. EP15157057.9, filed Feb. 27, 2015, the contents of which are incorporated herein by reference in its entirety.

FIELD OF THE INVENTION

The present invention relates to the field of generation of a composition of mesencephalic dopaminergic progenitor cells (MDAPCs) from a starting cell composition comprising pluripotent and/or multipotent stem cells. In particular, it relates to a reproducible method of generation of MDAPCs from a starting cell composition comprising pluripotent and/or multipotent stem cells which also allows an automation of said method.

BACKGROUND OF THE INVENTION

Parkinson's disease (PD) is characterized by the loss of midbrain dopaminergic neurons of the substantia nigra pars compacta (SNpc) and though to a lesser extent dopaminergic neurons of the ventral tegmental area (VTA). SN dopaminergic (DA) neurons project to the striatum and are crucial for locomotor control which is orchestrated by controlled release of dopamine from the projecting DA neurons. Loss of SNpc DA neurons is thought to cause the classical motor symptoms of this disease. However, motivational and affective impairments are also often observed in PD patients. These are usually attributed to a psychological reaction to the general motor impairment and to a loss of some of the neurons within the ventral tegmental area (VTA) (Drui et al., Mol Psychiatry. 2014 March; 19(3):358-67). During fetal development progenitors of these DA neurons are formed in the ventral neural tube of the developing mesencephalon. Progenitor cells from the so-called floor plate region are characterized by expression of the transcription factors FOXA2, Lmx1a and Otx2. These cells give rise to DA SNpc neurons and to DA VTA neurons. Fetal cells dissected form the developing mesencephalon and transplanted to the striatum of Parkinson patients could partially revert the Parkinson symptoms (Barker et al., Lancet Neurol. 2013 January; 12(1):84-91; Kefalopoulou et al., JAMA Neurol. 2014 January; 71(1):83-7). The limited availability of fetal DA progenitors or DA neurons has inspired the development of alternative methods for derivation of functionally equivalent cell populations from alternative sources. Pluripotent stem cells constitute such an alternative cell source. A recent study suggests that DA progenitors differentiated from embryonic stem cells might have the same features as cells derived from the human fetal ventral mesencephalon in terms of i) integration and projection capacity in a rat Parkinson model and ii) functional reversion of Parkinson symptoms (Grealish et al., Cell Stem Cell. 2014 6; 15(5): 653-65, Kirkeby et al., Cell Rep. 2012, 1(6):703-14).

Different methods have been reported to support in vitro differentiation of mixed populations of floor plate cells (Kirkeby et al., Cell Rep. 2012, 1(6):703-14; WO2013/067362A1; Doi et al., Stem Cell Reports. 2014 Mar. 6; 2(3):337-50). All protocols based on these publications are performed manually. Protocols comprise complex steps involving harvesting of adherent cells, dissociating cell clumps or embryoid bodies, seeding very defined and specific cell densities, frequent media changes, are conducted in either adherent or suspended culture conditions that may be varied or even alternate within the process.

It is known in the art that in vitro differentiated cell cultures do not constitute a homogenous cell population but may contain a plurality of cells with slightly different characteristics or differentiation stages. However, directed differentiation cultures optimized to generate floor plate cells are considered to contain mainly dopaminergic neuron progenitor cells but may also contain contaminating cells of any kind such as undifferentiated stem cells or a plurality of cells of unwanted differentiation fates such as serotonergic neurons.

Several markers have been disclosed that may serve to isolate subpopulations of dopaminergic progenitors from heterogeneous cell compositions at different time points after initiation of the differentiation process.

WO2013/067362A1 discloses a manually performed method to direct the lineage specific differentiation of human embryonic stem cells (hESC) and/or human induced pluripotent stem cells (hiPSC) into floor plate midbrain progenitor cells and then further into large populations of midbrain fate FOXA2+LMX1A+TH+dopamine (DA) neurons using novel culture conditions as well as CD142 as marker of authentic DA neurons. In contrast, MDAPCs do not express CD142.

Doi et al (Doi et al., Stem Cell Reports. 2014 Mar. 6; 2(3):337-50) described a method for isolation of dopaminergic progenitors using the surface marker corin identifying a subpopulation of cells derived from pluripotent stem cells. Unsorted and sorted corin+ cells were further cultivated and had shown to revert methamphetamine-induced rotation of the rats when transplanted 16 days after corin-based cell sorting. However, corin-based selection only enriches a subpopulation of mesenchephalic floor plate cells (Doi et al., Stem Cell Reports. 2014 Mar. 6; 2(3):337-50), as many FOXA2 positive cells are present in the corin-negative fraction at the day of sort.

WO2013/015457A1 discloses a manually performed method for selecting dopaminergic neuron progenitor cells which comprises detecting a marker specific for dopaminergic neuron progenitor cells. The markers were identified to be expressed in the corin subpopulation, resembling a subpopulation of the mesencephalic floor plate. The markers disclosed therein are markers selected from the group consisting of CD15 (SSEA-1), CD24, CD46, CD47, CD49b, CD57, CD58, CD59, CD81, CD90, CD98, CD147, CD184, Disalogangliosid GD2, SSEA-4, CD49f, SERINC4, CCR9, PHEX, TMPRSS1 IE, HTR1E, SLC25A2, Ctxn3, Cc17, Chrnb4, Chrna3, Kcnv2, Grm2, Syt2, Lim2, Mboat1, St3ga16, Slc39a12, Tacr1, Lrtm1 and Dscam, and/or the negativity of CD201. The preferred marker in this disclosure is Lrtm1 as it can be used together with conventional markers such as corin, Lmx1a, 65B13 and 18A5. Again, all markers disclosed therein are strongly associated to mesencephalic floor plate cells expressing corin, which are a part of mesencephalic floor plate cells only.

Kirkeby et al. (Kirkeby et al., Cell Rep. 2012, 1(6):703-14) were able to generate cell compositions with a high proportion of FOXA2-positive cells from human embryonic stem cells which can currently be regarded to be the most potent candidate cells for therapeutic treatment of Parkinson's disease, since they have been shown to be functionally equivalent to fetal ventral mesencephalic cells by Grealish et al. (Grealish et al., Cell Stem Cell. 2014 6; 15(5):653-65) using the same differentiation protocol as described in Kirkeby et al. (Kirkeby et al., Cell Rep. 2012, 1(6):703-14). Taken together, this analysis shows that hESC-DA neurons were indistinguishable from their fetal counterparts on the basis of graft appearance, morphology, and marker expression 6 months after grafting and that the hESC-derived grafts are rich in both A9-like (SNpc) and A10-like (VTA) DA neurons (Grealish et al., Cell Stem Cell. 2014 6; 15(5):653-65).

Cell compositions with a high proportion of FOXA2+ cells populations were used for these transplantation experiments. However, the degree of differentiation efficiencies reached in these studies rather represent the exception from the rule. It is known in the art that cultivation of a starting cell composition, i.e. pluripotent and/or multipotent stem cells, and the subsequent differentiation process is a highly sophisticated procedure which is subject to user-to-user variation and experimental outcome is influenced by slight variations, such as handling variations in general, density and/or concentration of cells, cytokines, small molecules or other substances used. It is also known in the art, that differentiation efficiency is highly cell-line dependent, i.e. different pluripotent stem cell lines do not exert the same response to the same differentiation protocol. Also experiment-to-experiment variations constitute a big hurdle for standardization of cell production for therapeutic use.

Therefore, there is a need in the art for a method to reproducibly generate a composition of cells, which can be used e.g. in clinical applications such as treatment of Parkinson's disease, wherein the cell composition comprises MDAPCs. This cell composition is the most promising candidate cell population for clinical use in the context of neurodegenerative diseases as it resembles the more complex composition of the ventral mesencephalon of post coitum week 6-7.5 human embryos Furthermore, generated MDAPCs which are intended to be used in cell therapy have to be produced under GMP or GMP-like conditions. Such a cell-manufacturing process requires extensive training of personnel as well as a dedicated infrastructure, which is a major obstacle to the wider use of these clinical procedures.

Current processes of developing compositions of mesencephalic dopaminergic progenitor cells for cellular therapies have until now been carried out manually.

Therefore, there is a need in the art for a method to reproducibly generate a composition of cells, which can be used e.g. in clinical applications such as treatment of Parkinson's disease, wherein the cell composition comprises MDAPCs.

All references cited herein, including patent applications and publications, are incorporated by reference in their entirety.

SUMMARY OF THE INVENTION

Unexpectedly, it was found that CD47 (Integrin associated protein, IAP) is a cell surface marker co-expressed with FOXA2 which can be used for a method for generation of a MDAPC composition from a starting cell composition which comprises pluripotent and/or multipotent stem cells. The use of said marker CD47 for the isolation of said MDAPCs allows to standardize (to make reproducible) the generation of such a composition of a population of CD47 expressing mesencephalic dopaminergic progenitor cells. The composition of MDAPC obtained by the methods of the present invention is more complex as it resembles the more complex composition of the ventral mesencephalon of post coitum week 6-7.5 human embryos than the compositions obtained by methods known in art to reproducibly generate subpopulations of mesencephalic dopaminergic progenitor cells such as methods using the marker corin or further differentiated authentic DA neurons using CD142.

Herein it is also disclosed that the methods of the present invention can be performed in a closed cell sample processing system (a closed system) resulting in MDAPCs generated under GMP or GMP-like conditions. Even more unexpectedly, it was found that the method of the present invention is accessible to an automated process using said closed cell sample processing system.

The cells of the composition obtained by the methods of the present invention may, for example, be used in cell replacement therapies for patients as a therapeutic treatment to ameliorate or reverse symptoms caused by the loss of dopamine neurons in a patient suffering from Parkinson's disease.

BRIEF DESCRIPTION OF THE FIGURES

FIG. 5

FIG. 6 shows sorting of CD47 positive cells with an indirect labeling strategy.

FIG. 7A shows immunofluorescence of the unsorted cell fraction with FOXA2 and LMX1A. FIG. 7B shows enrichment of FOXA2/LMX1A in the positive fraction after sorting of MDAPCs.

DETAILED DESCRIPTION OF THE INVENTION

Figure 1:
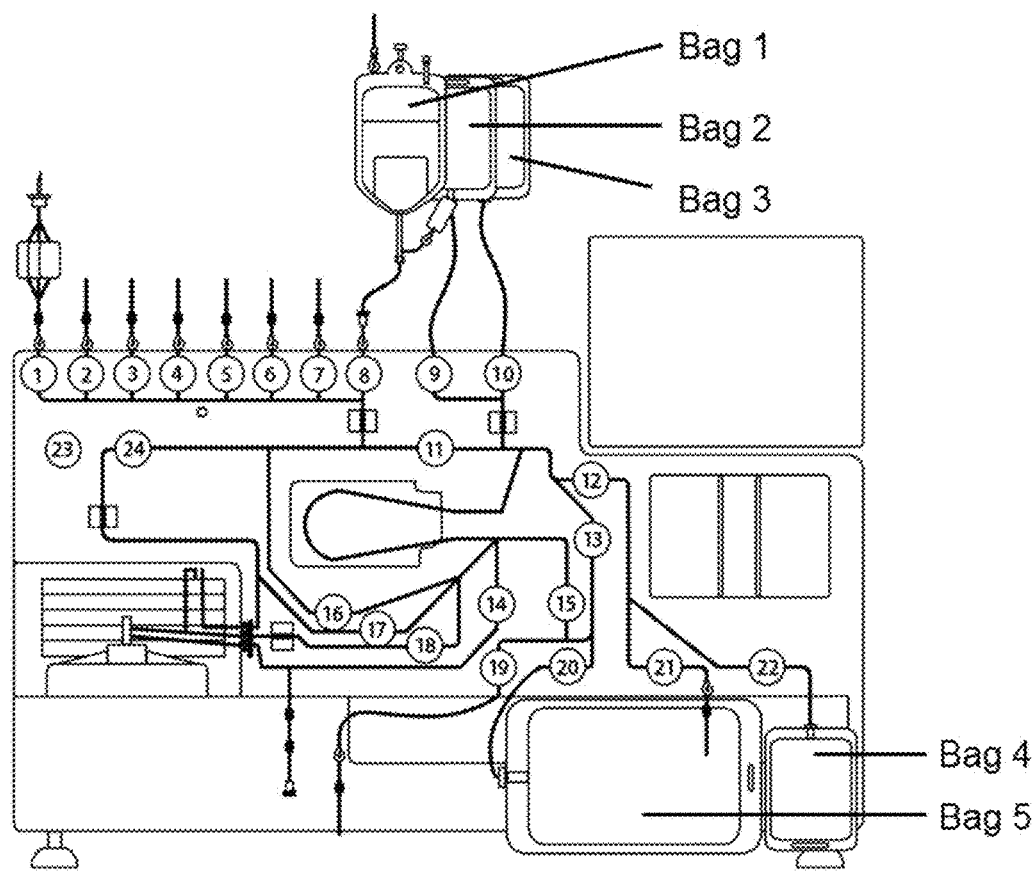
FIG. 1 shows a CliniMACS Prodigy TS730. Schematic drawing of the unmodified cultivation tubing set used for expansion and differentiation of iPSC.

Surprisingly, we found that CD47 expression is not only limited to a subpopulation of corin expressing cells, but shows the highest degree of correlation with respect to FOXA2-positive MDAPCs among 324 surface markers that were analyzed in a screening experiment. Therefore, CD47 can be used as marker for a method for a reproducible (and therefore standardized) generation of a cell composition of MDAPCs, which express CD47 on their cell surface (i.e. they are CD47 positive), for use e.g. in clinical applications, e.g. cell therapy such as treatment of Parkinson's disease from a starting cell composition, wherein said starting cell composition comprises pluripotent and/or multipotent stem cells. As the surface marker CD47 shows the highest degree of correlation with respect to FOXA2-positive mesencephalic dopaminergic progenitor cells among the 324 surface markers analyzed, a composition generated by the use of the marker CD47 for enrichment of the CD47+ cells from a starting cell composition comprising pluripotent and/or multipotent stem cells, wherein said stem cells have been differentiated to MDAPCs, is a more diverse cell composition compared to composition characterized by other known cell surface markers such as corin or others. The so far most commonly used mesencephalic dopaminergic progenitor cell marker corin leads to the enrichment of corin expressing mesencephalic floor plate cells which comprise a part of the MDAPCs only. The surface marker CD47 is superior compared to other cell surface markers of subpopulations of MDAPCs because it allows to separate a broader spectrum of cells resembling cells of the floor plate and of the basal plate immediately adjacent to the floor plate of post coitum week 6-7.5 human embryos. A benefit is expected if a cell composition of a more diverse mixture of MDAPCs (as obtained by the methods of the present invention) is used in clinical applications such as cell therapy such as treatment of Parkinson's disease compared to compositions which comprise a narrower composition of the MDAPCs such as e.g. generated by methods using the marker corin. The entirety (or the at least more complex or more diverse mixture) of subpopulations of MDAPCs can better interact among each other resulting in a better regeneration of the lost tissue in a patient suffering e.g. from Parkinson's disease which should be replaced by the application of cells during a cell therapy process.

The fact that CD47 can be used as marker for the generation of a complex or diverse MDAPC composition which concomitantly is a substantially pure composition of MDAPCs is more surprising particularly when it is taken into account that CD47 is a widespread molecule in the body in mammals such as humans.

In a first aspect the present invention provides a method for generation of a cell composition of mesencephalic dopaminergic progenitor cells from a starting cell composition comprising pluripotent and/or multipotent stem cells, the method comprising the steps of A) Differentiating said pluripotent and/or multipotent stem cells into mesencephalic dopaminergic progenitor cells, thereby generating a cell population comprising mesencephalic dopaminergic progenitor cells and other cells B) Dissociating the differentiated cells of step A) into a single cell suspension C) Enriching said mesencephalic dopaminergic progenitor cells by using an antigen binding molecule specific for the CD47 antigen for positive selection of said mesencephalic dopaminergic progenitor cells in said single cell suspension.

In another aspect the present invention provides a substantially pure composition of mesencephalic dopaminergic progenitor cells obtainable by the method of the present invention.

In a further aspect the present invention provides a pharmaceutical composition of mesencephalic dopaminergic progenitor cells obtainable by the method of the present invention and a pharmaceutical acceptable carrier.

Said compositions may comprise the cells isolated by the method of the present invention together with a label, i.e. the antigen-binding molecule attached to said cells. Alternatively, said cells of the composition are free of the label. Methods for dissociating a label, e.g. an antibody, from cells are well known in the art.

Embodiments

In a first embodiment of the present invention the method for generation of a cell population of mesencephalic dopaminergic progenitor cells from a starting cell composition, wherein said starting cell composition comprises pluripotent and/or multipotent stem cells, comprises the steps of:

a) differentiating said pluripotent and/or multipotent stem cells into mesencephalic dopaminergic progenitor cells, thereby generating a cell population comprising mesencephalic dopaminergic progenitor cells and other cells b) dissociating the differentiated cells of step a) into a single cell suspension c) contacting said single cell suspension with an antigen-binding molecule specific for the CD47 antigen, wherein said antigen binding molecule is coupled to a tag, thereby labeling the CD47 positive cells, d) isolating the labeled CD47 positive cells, i.e. the mesencephalic dopaminergic progenitor cells.

In one embodiment of present invention said method comprises a proliferation step of said pluripotent and/or multipotent stem cells before step a).

Often the amount of pluripotent and/or multipotent stem cells available is limited. A proliferation step can ensure that sufficient numbers of differentiated cells can be derived in order to achieve a therapeutic effective amount of cells for subsequent clinical application such as transplantation of these cells.

A proliferation step comprises culturing said pluripotent and/or multipotent stem cells in pluripotency conferring maintenance medium supporting undifferentiated expansion of pluripotent stem cells. Such media are well known to the person skilled in the art.

A differentiation step of said pluripotent stem and/or multipotent stem cells comprises adding differentiation inducing substances such as specialized cultivation media, cytokines, receptor antagonists or small molecules to the cultivation media. Also the cultivation matrix, i.e. the coating of the cell culture ware, may be used to bias the differentiation process by providing different proteins or chemical compounds that are in contact with the cells. Such substances are well known to the person skilled in the art.

Said dissociating step for dissociating the cells can be performed by mechanical means, enzymatic and/or chemical agents. Such processes for dissociating cells are well known to the person skilled in the art.

Steps c) ("contacting") and d) ("isolating") can be performed in combination using e.g. fluorescent-activated cell sorting using a flow sorter or magnetic cell sorting. Such processes for separating cells from other cells are well known in the art.

In one embodiment of the invention said method is performed in a closed cell sample processing system.

Some or all steps a) to d) and optionally the proliferation step before step a) may be performed in a closed cell sample processing system which allows to operate under GMP or GMP-like conditions resulting in compositions which are clinically applicable.

The closed cell sample processing system may be any system which reduces the risk of cell culture contamination while performing culturing processes in a closed system under sterile conditions so that the cells subsequently are applicable to a patient.

In one embodiment of the invention said method is an automated method (process).

The robust expression of CD47 on the surface of the mesencephalic dopaminergic progenitor cells could surprisingly be exploited to establish an automated process in a closed cell sample processing system. Other mesencephalic dopaminergic progenitor cell markers found in our screen or previously described such as corin, CD142, or SSEA4 are not or less suitable or even counterproductive as i) they have no robust expression of the marker on the cell surface of the mesencephalic dopaminergic progenitor cells, and/or ii) they are restricting the cell population to an unwanted extend (corin), iii) and/or can not be used for an early sorting (CD142), iv) and/or are even enriching for pluripotent cells which is something which should absolutely be avoided (SSEA4). Pluripotent stem cells, when transplanted into patients may form teratomas displaying uncontrolled growth leading to tissue injury and bear the risk of malignant disease progression. Therefore, all steps resulting in a better defined cell composition, free of contaminating pluripotent cells, help to increase safety and efficacy of a clinical application of the cell composition such as a potential cell product for treatment of Parkinson's Disease.

A timely sorting of target cells (i.e. between day 9 and 16 post in vitro differentiation, preferentially between day 11 and 16, more preferentially day 16) is advantageous as at later time points i) the plasticity of neurons in terms of ability to form processes and to interconnect into the existing neuronal network of a recipient and ii) the possibility to harvest cells without harm from a dish where they have attached using automatable procedures is dramatically reduced.

In another embodiment of the invention the dissociation step of said differentiated cells is performed by passing the cell suspensions through one or more cell strainer(s) wherein the pore size ranges from 200 µm to 20 µm and if more than one strainer is used the pore size of each strainer may be identical in all strainers, identical to the preceding strainer and/or smaller than the preceding strainer, thereby generating a single cell suspension. Preferentially, said dissociation step is performed in said closed cell sample processing system. More preferentially, said dissociation step is performed in said closed cell sample processing system and is performed automatically.

Such a closed cell sample processing system may be able to perform most, preferentially all steps mentioned above in an automated manner. Exemplarily the CliniMACS Prodigy® (Miltenyi Biotec GmbH, Germany) is used herein as a closed cell sample processing system on which an automated process was implemented. This system is disclosed in WO2009/072003 in detail. But it is not intended to restrict the use of the method of the present invention to the CliniMACS Prodigy®.

The closed cell sample processing system may comprise a plurality of tubing sets (TS) where cells are transferred between TS by sterile docking or sterile welding.

Figure 2:
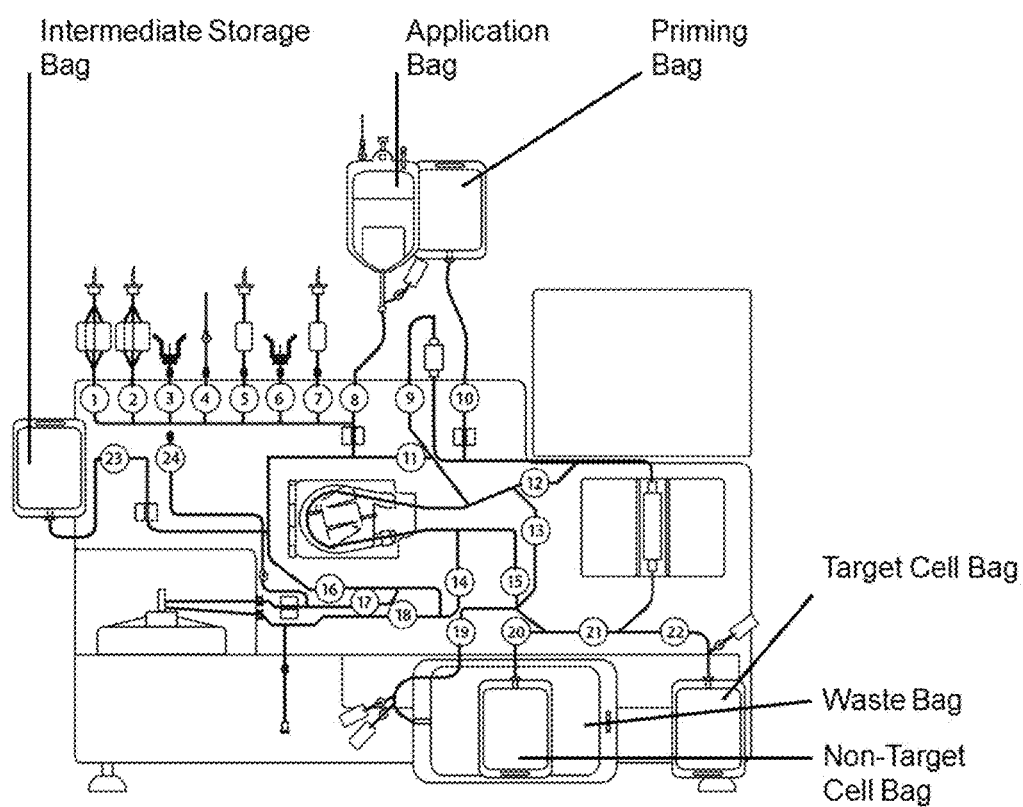
FIG. 2 shows a CliniMACS Prodigy TS510. Schematic drawing of the tubing set used for immunomagnetic separation of differentiated MDAPCs.

Different modules of the process may be performed in different functionally closed TS with transfer of the product (cells) of one module generated in the one tubing set to another tubing set by sterile means. For example, pluripotent cells can be expanded and differentiated into compositions comprising mesencephalic dopaminergic progenitor cells in a first tubing set TS730 (FIG. 1) by Miltenyi Biotec GmbH and the harvested and/or dissociated cells be transferred to a second tubing set by welding off TS730 and welding onto second tubing set TS510 (FIG. 2) by Miltenyi Biotec GmbH for further magnetic isolation of subpopulations from said cell compositions, washing and optionally formulation for later cryopreservation.

The closed cell sample processing system may comprise a) a sample processing unit comprising an input port and an output port coupled to a rotating container (or centrifugation chamber) having at least one sample chamber, wherein the sample processing unit is configured to provide a first processing step to a sample or to rotate the container so as to apply a centrifugal force to a sample deposited in the chamber and separate at least a first component and a second component of the deposited sample; and b) a sample separation unit coupled to the output port of the sample processing unit, the sample separation unit comprising a separation column holder, a pump, and a plurality of valves configured to at least partially control fluid flow through a fluid circuitry and a separation column positioned in the holder, wherein the separation column is configured to separate labeled and unlabeled components of sample flown through the column.

Said rotating container may also be used as a temperature controlled cell incubation and cultivation chamber (CentriCult Unit=CCU). This chamber may be flooded with defined gas mixes, provided by an attached gas mix unit (e.g. use of pressurized air/N2/CO2 or N2/CO2/O2).

The closed cell sample processing system may also comprise attached and sterilely connected cultivation spaces such as cultivation bags, cultivation bags with a multiplicity of stacked cultivation layers or flasks or multilayered flasks which can be independently incubated in external controlled cell incubation chambers (gas and heat controlled). Additionally, the closed cell sample processing system may comprise a heat exchange unit for controlling and adjusting the temperature of culture media, buffers or other liquids which are pumped through the closed system.

All reagents may be connected to the closed system before process initiation. This comprises all buffers, solutions, cultivation media and supplements, MicroBeads, used for washing, transferring, suspending, cultivating, harvesting cells or immunomagnetic cell sorting within the closed system. Alternatively, such reagents might by welded or connected by sterile means at any time during the process.

In one embodiment of the invention in said method with steps a) to d) (and optionally the proliferation step before step a)) said antigen binding molecule specific for the CD47 antigen is an anti-CD47 antibody or fragment thereof.

In one embodiment of the invention in said method with steps a) to d) (and optionally the proliferation step before step a)) said tag is a fluorophore if step d) is performed by fluorescent-activated cell sorting using a flow sorter such as FACSAria™ (BD Biocsiences) or MoFlo™ XDP (Beckman Coulter) or MACSQuant® Tyto™ (Miltenyi Biotec GmbH), or said tag is a magnetic particle if step d) is performed using magnetic cell sorting such as MACS® (Miltenyi Biotec GmbH).

In a further embodiment of the present invention the method for generation of a population of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cells,
b) dissociating the differentiated cells of step a) into a single cell suspension
c) contacting said single cell suspension with an antigen binding molecule specific for a pluripotent stem cell surface marker wherein said antigen binding molecule is coupled to a magnetic particle, thereby labeling cells expressing said pluripotent stem cell marker; and
d) magnetically separating the labeled cells of c), thereby generating a cell composition depleted of cells positive for a pluripotent stem cell surface marker
e) contacting the cell composition of d) with an antigen-binding molecule specific for the CD47 antigen, wherein said antigen binding molecule is coupled to a magnetic particle, thereby labeling the CD47 positive cells, and
f) magnetically separating the labeled CD47 positive cells, thereby generating a cell composition enriched for mesencephalic dopaminergic progenitor cells.

Alternatively, said step e) may be performed before said step d) but after step b).

In a further embodiment of the present invention the method for generation of a population of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cellsb) dissociating the differentiated cells of step a) into a single cell suspension
c) contacting said single cell suspension with an antigen binding molecule specific for a pluripotent stem cell surface marker wherein said antigen binding molecule is coupled to a magnetic particle, thereby labeling cells expressing said pluripotent stem cell marker; and
d) magnetically separating the labeled cells of c), thereby generating a cell composition depleted of cells positive for a pluripotent stem cell surface marker
e) contacting cell composition of d) with an antigen-binding molecule specific for the CD47 antigen, wherein said antigen binding molecule is coupled to a hapten, thereby labeling the CD47 positive cells,
f) contacting the cell composition of e) with an antigen binding molecule specific for said hapten wherein said antigen binding molecule is coupled to a magnetic particle, thereby labeling the cells of e) that have been labeled with said antigen-binding molecule specific for the CD47 antigen; and
g) magnetically separating the labeled CD47 positive cells, thereby generating a cell composition enriched for mesencephalic dopaminergic progenitor cells.

Alternatively, said step e) may be performed before said step d) but after step b).

In a further embodiment of the present invention the method for generation of a population of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cells
b) dissociating the differentiated cells of step a) into a single cell suspension
c) contacting said single cell suspension with an antigen binding molecule specific for a pluripotent stem cell surface marker wherein said antigen binding molecule specific for a pluripotent stem cell surface marker is coupled to a first hapten, thereby labeling cells expressing said pluripotent stem cell marker, and contacting cell said composition with an antigen-binding molecule specific for the CD47 antigen, wherein said antigen binding molecule specific for the CD47 antigen is coupled to a second hapten, thereby labeling the CD47 positive cells
d) contacting the cell composition of c) with an antigen binding molecule specific for said first hapten wherein said antigen binding molecule specific for said first hapten is coupled to a magnetic particle, thereby labeling cells of c) that have been labeled with said antigen-binding molecule specific for a pluripotent stem cell surface marker, and contacting the cell composition of c) with an antigen binding molecule specific for said second hapten wherein said antigen binding molecule specific for said second hapten is coupled to a magnetic particle, thereby labeling cells of c) that have been labeled with said antigen-binding molecule specific for the CD47 antigen, and
e) magnetically separating said labeled pluripotent stem cell marker positive cells, thereby generating a cell composition depleted of cells positive for a pluripotent stem cell surface marker; and
f) magnetically separating the labeled CD47 positive cells, thereby generating a cell composition enriched for mesencephalic dopaminergic progenitor cells,
wherein the first and second hapten may be different haptens and wherein the magnetic particle used for labeling the first hapten is distinguishable from the magnetic particle used for labeling the second hapten, such as MACSiBeads™ and MACS® MicroBeads (both Miltenyi Biotec GmbH).

In a further embodiment of the present invention the method for generation of a cell composition of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cells,
b) dissociating the differentiated cells of step a) into a single cell suspension
c) contacting said single cell suspension with an antigen binding molecule specific for a pluripotent stem cell surface marker wherein said antigen binding molecule is coupled to a first hapten, thereby labeling cells expressing said pluripotent stem cell marker
d) contacting the cell composition of c) with an antigen binding molecule specific for said first hapten wherein said antigen binding molecule specific for said first hapten is coupled to a magnetic particle, thereby labeling cells of c) that have been labeled with said antigen-binding molecule specific for a pluripotent stem cell surface marker, e) magnetically separating said labeled pluripotent stem cell marker positive cells, thereby generating a cell composition depleted of cells positive for a pluripotent stem cell surface marker; and
f) contacting said depleted cell composition of e) with an antigen-binding molecule specific for the CD47 antigen, wherein said antigen binding molecule is coupled to a magnetic particle, thereby labeling the CD47 positive cells, and
g) magnetically separating the labeled CD47 positive cells, thereby generating a cell composition enriched for mesencephalic dopaminergic progenitor cells.

Step f) may be performed before step e) but after step b) if the magnetic particle of said antigen binding molecule specific for said first hapten and the magnetic particle of said antigen-binding molecule specific for the CD47 antigen are distinguishable magnetic particle such as MACSiBeads™ and MACS® MicroBeads (both Miltenyi Biotec GmbH).

In a further embodiment of the present invention the method for generation of a cell composition of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cells,
b) dissociating the differentiated cells of step a) into a single cell suspension
c) contacting said single cell suspension with an antigen binding molecule specific for a pluripotent stem cell surface marker wherein said antigen binding molecule is coupled to a magnetic particle, thereby labeling cells expressing said pluripotent stem cell marker; and
d) magnetically separating the labeled cells of c), thereby generating a cell composition depleted of cells positive for a pluripotent stem cell surface marker
e) contacting said depleted cell composition of d) with an antigen-binding molecule specific for the CD47 antigen, wherein said antigen binding molecule is coupled to a fluorophore thereby labeling the CD47 positive cells,
f) separating the labeled CD47 positive cells by fluorescent activated cell sorting, thereby generating a cell composition enriched for mesencephalic dopaminergic progenitor cells Alternatively, said step e) may be performed before said step d) but after step b).

In a further embodiment of the present invention the method for generation of a cell composition of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells, thereby generating a cell population comprising mesencephalic dopaminergic progenitor cells and other cells
b) dissociating the differentiated cells of step a) into a single cell suspension
c) contacting said single cell suspension with an antigen binding molecule specific for a pluripotent stem cell surface marker wherein said antigen binding molecule is coupled to a magnetic particle, thereby labeling cells expressing said pluripotent stem cell marker; and
d) magnetically separating the labeled cells of c), thereby generating a cell composition depleted of cells positive for a pluripotent stem cell surface marker
e) contacting said depleted cell composition of d) with an antigen-binding molecule specific for the CD47 antigen, wherein said antigen binding molecule specific for the CD47 antigen is coupled to a hapten thereby labeling the CD47 positive cells,
f) contacting the cell composition of e) with an antigen binding molecule specific for said hapten wherein said antigen binding molecule specific for said hapten is coupled to a fluorophore, thereby labeling the cells of e) that have been labeled with said antigen-binding molecule specific for the CD47 antigen, and
g) separating the labeled CD47 positive cells by fluorescent activated cell sorting, thereby generating a cell composition enriched for mesencephalic dopaminergic progenitor cells.

Alternatively, step e) may also be performed before step d) but after step c). Then step f) may also be performed before step d) and after step e) and step g) may also be performed before step d).

In a further embodiment of the present invention the method for generation of a cell composition of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells; thereby generating a cell population comprising mesencephalic dopaminergic progenitor cells and other cells
b) dissociating the differentiated cells of step a) into a single cell suspension
c) contacting said single cell suspension with an antigen binding molecule specific for a pluripotent stem cell surface marker wherein said antigen binding molecule specific for a pluripotent stem cell surface marker is coupled to a first hapten, thereby labeling cells expressing said pluripotent stem cell marker
d) contacting the cell composition of c) with an antigen binding molecule specific for said first hapten of wherein said antigen binding molecule specific for said first hapten is coupled to a magnetic particle, thereby labeling cells of c) that have been labeled with said antigen-binding molecule specific for a pluripotent stem cell surface marker,
e) magnetically separating said labeled pluripotent stem cell marker positive cells, thereby generating a cell composition depleted of cells positive for a pluripotent stem cell surface marker; and
f) contacting said depleted cell composition of d) with an antigen-binding molecule specific for the CD47 antigen, wherein said antigen binding molecule specific for the CD47 antigen is coupled to a second hapten thereby labeling the CD47 positive cells,
g) contacting the cell composition of f) with an antigen binding molecule specific for said second hapten wherein said antigen binding molecule specific for said second hapten is coupled to a fluorophore, thereby labeling the cells of f) that have been labeled with said antigen-binding molecule specific for the CD47 antigen, and
h) separating the labeled CD47 positive cells by fluorescent activated cell sorting, thereby generating a cell composition enriched for mesencephalic dopaminergic progenitor cells.

Alternatively, step f) may also be performed before step e) but after step d). Then step g) may also be performed before step e) and after step d) and step h) may also be performed before step e).

In a further embodiment of the present invention the method for generation of a cell composition of mesencephalic dopaminergic progenitor cells from a starting cell composition, wherein said starting cell composition comprises pluripotent and/or multipotent stem cells, comprises the steps of:
a) differentiating said pluripotent and/or multipotent stem cells into mesencephalic dopaminergic progenitor cells; thereby generating a cell population comprising mesencephalic dopaminergic progenitor cells and other cells,
b) dissociating the differentiated cells of step a) into a single cell suspension
c) contacting said single cell suspension with an antigen binding molecule specific for a pluripotent stem cell surface marker wherein said antigen binding molecule specific for a pluripotent stem cell surface marker is coupled to a first hapten, thereby labeling cells expressing said pluripotent stem cell marker
d) contacting the cell composition of c) with an antigen binding molecule specific for said first hapten of wherein said antigen binding molecule specific for said first hapten is coupled to a magnetic particle, thereby labeling cells of c) that have been labeled with said antigen-binding molecule specific for a pluripotent stem cell surface marker,
e) magnetically separating said labeled pluripotent stem cell marker positive cells, thereby generating a cell composition depleted of cells positive for a pluripotent stem cell surface marker; and
f) contacting said depleted cell composition of e) with an antigen-binding molecule specific for the CD47 antigen, wherein said antigen binding molecule specific for the CD47 antigen is coupled to a fluorophore thereby labeling the CD47 positive cells,
g) separating the labeled CD47 positive cells by fluorescent activated cell sorting, thereby generating a cell composition enriched for mesencephalic dopaminergic progenitor cells.

Alternatively, step f) may also be performed before step e) and after step b). Then step g) may also be performed before step e).

The antigen binding molecule specific for a pluripotent stem cell marker may be selected from the group consisting of SSEA4, UEA-1, SSEA-3, Tra-1-60, Tra-1-81, SSEA-5, CD90 and CD30.

Preferentially, the antigen binding molecule specific for a pluripotent stem cell marker may be SSEA4 or UEA-1.

Said different tag may be a different fluorophore (compared to the first used fluorophore in said method) if step d) is performed by a flow cytometric method, or wherein said different tag may be a different magnetic bead (compared to the first used magnetic bead in said method) if step d) is performed by a magnetic cell separation method.

The mesencephalic dopaminergic progenitor cells used in the method of the present invention may be human or non-human primate cells.

In the following the steps of the methods of the present invention and the materials needed for performing said methods are explained in more detail with focus on the implementation on a closed cell sample processing system, preferentially in an automated manner as this is a preferred embodiment of the invention. But no limitation to a method in a closed cell sample processing system is intended.

Before starting the steps of the present method a starting cell composition must be provided. Said starting cell composition may comprise pluripotent and/or multipotent stem cells. Preferentially said starting cell composition may comprise cells, wherein said cells are selected from the group consisting of non-embryonic stem cells, embryonic stem cells, induced pluripotent stem cells or lineage committed stem or progenitor cells such as neural stem cells (NSCs) or LT-NES® cells. More preferentially, said cells are induced pluripotent stem cells (iPS cells). Most preferentially said iPS cells are human iPS cells.

Starting cell compositions may be provided in transfer bags or other suited containers which can be connected to the closed system by sterile means. Cells can then be transferred to the CCU for washing or seeding in preparation for subsequent cultivation within the CCU or in attached cultivation spaces.

All media, buffers, reagents, supplements, MicroBead solutions may be provided at final working concentrations but may also be provided as higher concentrated stock solutions (e.g. 1.5×, 2×, 10×, 50×). All buffer or cultivation media exchanges or additions are carried out automatically within the closed system.

Pluripotent maintenance cultures: Cultivation, i.e. expansion of the starting cell material may be achieved as adherent cultures on suitable matrices selected from the group consisting of vitronectin or vitronectin variants, fibronectin or variants thereof, Laminin-511-, -521, -421, -411, -111, -211, -332, Poly-ornithine/Laminin/Fibronectin, E-Cadherin-ectodomains, or recombinant Laminin subdomains (such as Laminin-511-E8), protein targeting domains such as antibodies, Matrigel™, Geltrex™, Cellstart™, Synthemax™ or variants thereof, peptides or synthetic polymers.

Cells may be maintained in pluripotency conferring maintenance medium supporting undifferentiated expansion of pluripotent stem cells (e.g. STEMMACS-iPS-Brew™, Essential8™, mTES1™, mTESR2™, TESR-E8™, StemPro™, NutriStem™, or alternative media). Induction of differentiation may be initiated by simply exchanging the cultivation medium from pluripotency conferring maintenance medium to differentiation inducing medium, or by first harvesting of cells, i.e. release of cells or cell colonies form the cultivation surface or matrix followed exposure to differentiation inducing conditions. Harvest of cells can be obtained by medium or buffer comprising chelating molecules known to break up ion-dependent cell-cell interactions (such as EDTA, Citrate, EGTA), enzymes or enzyme mixes such as but not limited to Trypsin, Trypsin-EDTA, TrypLE™, TrypLE™-Select, TrypLE-Express™, Dispase, Papain, Accutase, Accumax, Collagenases, Liberase resulting in either cell clusters, cell aggregates down to even oligomeric or dimeric cell clusters or even single cell suspensions. Cells may also be reseeded for multiple rounds of expansion either within the CCU or culture bags.

When using multipotent stem cells such as NSCs, LT-NES® or other expandable cells of lower potency than pluripotent stem cells alternative media are to be used to ensure maintenance of stem cells.

Cells may also be expanded in aggregates as suspension cultures. Therefore, the surface of the cell culture ware may be prepared to confer reduced cell attachment (e.g. by coating with Polyhydroxyethylmethacrylate (PHEMA) or alternative substances known to reduce cell attachment to plastic surfaces. Additionally, the CCU may be rotated at different negative and positive revolutions per/min in different intervals which in combinations constitutes a "cultivation program". Said movement might be regarded as another means to reduce unwanted cell attachment in the suspension culture process. Furthermore special media additives might be used to confer floating cell aggregates as reported by Otsuji et al (Stem Cell Reports. 2014 Apr. 24; 2(5):734-45), as well as other known substances known to reduce shear stress in rotated or stirred suspension cultures. Alternatively, suspension cultures may be initiated and maintained in sterilely connected cultivation bags such as but not limited to highly gas permeable silicon bags that are kept in controlled cell incubators (gas and heat controlled) and may be agitated using specially suited rocking devices.

Figure 3:
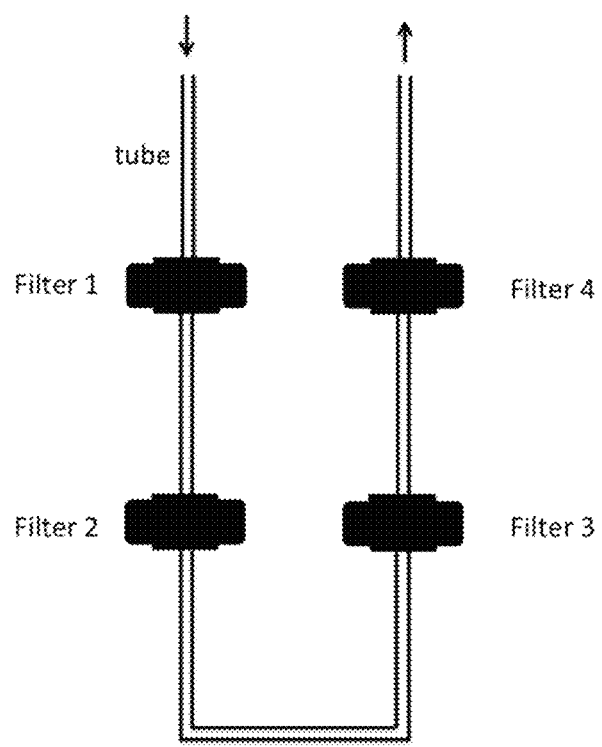
FIG. 3 shows a drawing of a cell dissociation loop consisting of a cascade of strainer units sterilely connected to the tubing set. Cells can be passed through one strainer or strainer cascade. Strainer pore size can be the same for each strainer (i.e. e.g. 100 µm for Strainer 1-4) or variable (i.e. e.g. 200 µm for Strainer 1, 100 µm for Strainer 2, 70 µm for Strainer 3, 30 µm for Strainer 4). Number of strainers can range from 1 to 5.
Figure 4A:
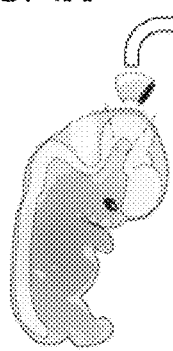
FIG. 4A shows the human mesencephalon at PC week 7.5.
Figure 4B:
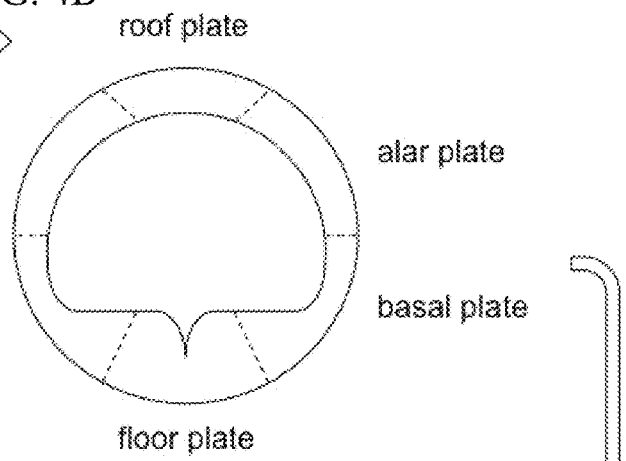
FIG. 4B shows a schematic drawing of the human coronal sectioned neural tube of the mesencephalon. The neural tube can be subdivided into four longitudinal domains along the ventro-dorsal axis. The most ventral part of the neural tube is called the floor plate and the most dorsal part forms the roof plate.
Figure 4C:
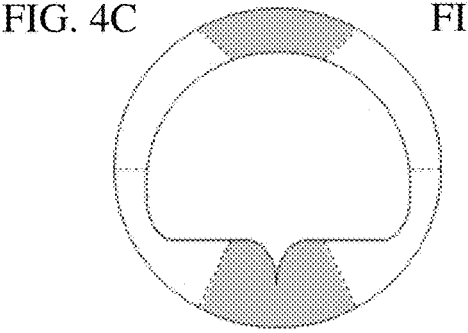
FIG. 4C is a drawing indicating the protein expression in the human mesencephalon of LMX1A, which is expressed in the roof and floor plate.
Figure 4D:
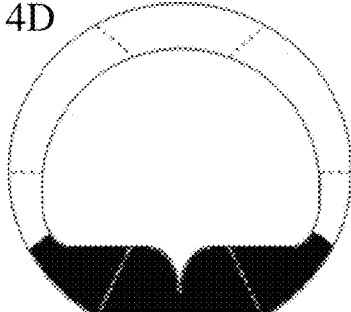
FIG. 4D is a drawing indicating the protein expression in the human mesencephalon of FOXA2, which is expressed also laterally of the floor plate into the so called basal plate.

Cell harvest may involve centrifugation steps within the CCU. Cell suspensions may also be passed through one or more strainer units with identical or decreasing pore size (200-20 µm) within the system in order to dissociate/break down cell aggregates and or remove unwanted cell clusters (FIG. 3). Alternatively, cells may be pumped into sterilely connected gentleMACS dissociation tubes for subsequent mechanical dissociation using the gentleMACS or gentleMACS-Octo™ device (Miltenyi Biotec GmbH). Alternatively, cells may be transferred to a cell transfer bag and processed manually to achieve dissociation of cell aggregates/cell clusters, e.g. by trituration using pipettes or needles with or without additional filtration steps under sterile conditions. Cells can then be retransferred into the closed system as described before.

Samples of media, buffers or cell suspensions can be automatically transferred to sample pouches or sample loops allowing for sampling steps throughout the process. Sample pouches maybe welded off for manual downstream analysis of the contained solutions.

In order to generate differentiated MDAPCs starting cell compositions such as pluripotent and/or multipotent stem cells may be exposed to differentiation inducing conditions as disclosed e.g. in (Kirkeby et al., Cell Rep. 2012, 1(6): 703-14, Kriks et al., Nature. 2011 6; 480(7378):547-51, Doi et al., Stem Cell Reports. 2014 Mar. 6; 2(3):337-50). Cells can be differentiated either as adherent or suspension cultures.

For adherent cultures cells may be differentiated with or without previous expansion of undifferentiated (pluripotent and/or multipotent) stem cells. For the former case cells can be differentiated in the same culture compartment (CCU or bag) used for expansion of the undifferentiated stem cells or (re-)plated into a new compartment (CCU or bag). For differentiation cultivation matrices as outlined for pluripotent maintenance culture or alternative matrices may be used. For the latter case cells can be directly exposed to differentiation conditions without previous expansion of the stem cells. For suspension cultures cells may either be cultivated in the CCU or in attached cell bags as outlined for pluripotent maintenance cultures. For all differentiation cultures one or more different differentiation media may be used during the process.

Differentiation of cells into MDAPCs may take between 9 and 20 days depending on the protocol used. In one embodiment of the invention cells are differentiated for 10 to 20 days, more preferably between day 11 and day 16, most preferably 16 days using modified differentiation conditions e.g. to those disclosed in Kirkeby et al. (Kirkeby et al., Cell Rep. 2012, 1(6):703-14) or Kriks et al. (Nature. 2011 6; 480(7378):547-51). Early mesencephalic dopaminergic progenitor cells (day 10-day 16) may either be seeded at very high density (10,000-15,000 cells/µl), i.e. between 100,000 and 1,500,000 cells per cm$^2$, either with or without addition of Rho-kinase inhibitors such as Y-27632, Thiazovivin, HA1077 (Fasudil) or alternative substances preventing hypercontraction of the cells after dissociation and during subsequent culture initiation (such as but not limited to blebbistatin). Cells may be differentiated as adherent culture throughout the process, as suspended aggregate cultures or in adherent and suspended culture whereas change of these two cultivation modes may be changed back and forth and starting with either adherent or suspended cultures. Media components may be exchanged to meet the regulatory requirements of GMP cell manufacturing. Furthermore, choice and concentrations of cytokines and small molecules may be varied to ensure differentiation to MDAPCs. Furthermore, matrices might be chosen from but not limited to vitronectin or vitronectin variants, fibronectin or variants thereof, Laminin-511-, -521, -421, -411, -111, -211, -332, Poly-ornithine/Laminin/Fibronectin, E-Cadherin-ectodomains, or recombinant Laminin subdomains, protein targeting domains such as antibodies, Matrigel™, Geltrex™, Cellstart™, Synthemax™ or variants thereof, peptides or synthetic polymers.

After differentiation, selection of MDAPCs based on surface markers may be carried out automatically either in the same TS or after transfer of cells to a new TS at different time points during the automatic cultivation procedure. As mentioned above, different markers have been disclosed to be expressed on subpopulations of MDAPCs.

Cells may also be automatically prepared for cyropreservation, whereby at any time during the process, cell suspensions or suspended cell clusters are concentrated within the CCU and resuspended in a suitable cryopreservation solution. The cells may then be automatically be transferred into cryopreservation bags, welded off and subjected to a controlled rate freezing process.

Definitions

Unless defined otherwise, technical and scientific terms used herein have the same meaning as commonly understood by one of ordinary skill in the art to which this invention belongs.

The term "pluripotent stem cell" as used herein refers to cells being capable to self renew and have the potential to differentiate into any of the embryonic germ layers endoderm, mesoderm and ectoderm and cells derived from this. These criteria hold true for embryonic stem cells (ESC) and induced pluripotent stem cells (iPSC). Preferentially these cells are human. Different degrees of pluripotency are known in the art, referred to as "primed state" pluripotent stem cells, "naive state" pluripotent stem cells or "reset stage" pluripotent stem cells.

The term "induced pluripotent stem cells (iPSC)" as used herein refers to pluripotent cells generated by conversion of cells of lower potency, i.e. more differentiated cells, typically a somatic cell, to a state of pluripotency, the resulting cells being capable to self renew and having the potential to differentiate into any of the embryonic germ layers endoderm, mesoderm and ectoderm and cells derived from this. Reprogramming may be achieved by methods such as nuclear transfer, cell fusion, or factor induced reprogramming, i.e. induced expression of one or more reprogramming factors, such as but not limited to OCT4, SOX2, KLF4, C-MYC, NANOG, LIN28, etc. Reprogramming factors may be introduced as nucleic acids, or proteins by viral transduction or by transfection. Different culture conditions and reprogramming factor combinations may result in different degrees of pluripotency, referred to as "primed state" pluripotent stem cells, "naive state" pluripotent stem cells or "reset stage" pluripotent stem cells.

The term "multipotent stem cell" as used herein refers to progenitor cells that have the capacity to differentiate into multiple but limited cell types.

The term "neural stem cell" (NSC) as used herein refers to self-renewing, multipotent cells that generate the main cell types of the nervous system. NSCs primarily differentiate into neurons, astrocytes, and oligodendrocytes. In vitro NSCs can also be propagated under self renewing conditions, wherein cells undergo symmetric cell divisions resulting two non-specialized daughter cells.

Figure 5A:
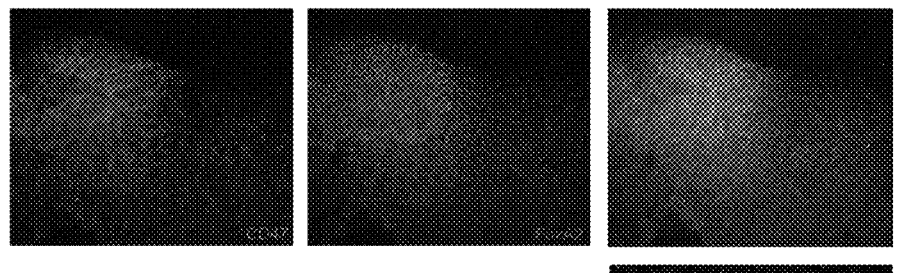
FIG. 5A shows immunofluorescence of MDAPCs.
Figure 5B:
FIG. 5B shows flow cytometric analyses of the MDAPCs which show the correlation of CD47 and FOXA2 and FIG. 5C shows the staining of CD47 and corin.
Figure 5C:
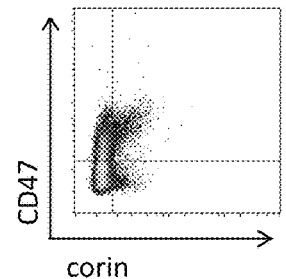

The term "mesencephalic dopaminergic progenitor cells (MDAPCs)" as used herein refers to in vitro differentiated cells characterized by expression of CD47 and FOXA2, whereby >50%, 60%, 70%, 80%, 90%, 95%, 96%, 97%, 98%, 99% or 100% of said FOXA2+ cells co-express LMX1A, the composition resembling in vivo mesencephalic FOXA2+ cells of the floor plate and FOXA2+ cells of the basal plate immediately adjacent to the floor plate of post coitum week 6-7.5 human embryos (FIG. 4). MDAPCs comprise corin expressing cells and corin negative cells, reflecting that corin expressing cells represent only a minor fraction of all MDAPCs (FIG. 5C). MDAPCs do not express CD142, a marker associated with authentic DA neurons, which represents a later stage of differentiation and maturation and is associated with co-expression of Nurr1, which is also not expressed by MDAPCs.

The term "cell composition of mesencephalic dopaminergic progenitor cells (MDAPCs)" as used herein refers to a cell composition comprising CD47 expressing mesencephalic progenitor cells co-expressing FoxA2, and CD47 expressing cells which do not co-express FOXA2, wherein >70%, 80%, 90%, 95%, 96%, 97%, 98%, 99% or 100% of CD47 expressing cells co-express FOXA2.

Cells may be derived in vitro from different starting cell compositions such as but not limited to embryonic stem cells, induced pluripotent stem cells, primary neural cells from embryonic or fetal midbrain or in vitro generated expandable neural stem cell lines or LTNES®.

The term "differentiation" as used herein refers to cellular differentiation, a term used in developmental biology, and describes the process by which a less specialized cell becomes a more specialized cell type. In vitro, differentiation of stem cells can occur spontaneously or is induced intentionally by adding differentiation inducing substances such as specialized cultivation media, cytokines, receptor antagonists or small molecules to the cultivation media. Also the cultivation matrix, i.e. the coating of the cell culture ware, may be used to bias the differentiation process by providing different proteins or chemical compounds that are in contact with the cells.

The term "single cell suspension" as used herein refers to a cell suspension, wherein cells from a solid tissue or cell clusters from an in vitro cell culture have been separated from each other and maintained separated from each other. It is not contrary to the meaning of the term "single cell suspension" that a low percentage of cells may adhere to each other. Single cell suspension can be achieved by any mechanical, enzymatic or chemical means. Methods therefore are well known in the art and are partly disclosed herein. Important is that the single cell suspension achieved by such dissociating methods is capable for use in subsequent processes such as cell sorting.

The term "starting cell composition" as used herein refers to a sample comprising pluripotent or multipotent stem cells and other cells in any ratio or a mixture of said pluripotent or multipotent stem cells to the other cells in that sample. Said other cells may be spontaneously differentiated cells originating from said pluripotent or multipotent stem cells. Said spontaneously differentiated cells are characterized by loss of expression of stem cell associated markers and initiation of expression of differentiation associated markers. Preferentially, the portion of said other cells within the starting cell compositions may not exceed 30%, 20%, 10%, 9%, 8%, 7%, 6%, 5%, 4%, 3%, 2%, 1% of all cells. Preferentially, the cells are viable. The cells may be originated from humans or animals, especially mammals including but not limited to mouse, rats, pigs, cattle, dog, monkey. Cells of tissue derived from adult brains, parts of adult brains, embryonic or fetal tissue can also be used. Furthermore, or in vitro generated expandable neural stem cell lines (NSCs) or LT-NES® may be used.

The term "marker" as used herein refers to a cell antigen that is specifically expressed by a certain cell type. Preferentially, the marker is a cell surface marker so that enrichment, isolation and/or detection of living cells can be performed. The markers may be positive selection markers such as CD47 as disclosed herein or may be negative selection markers such as SSEA4 as used herein. Cell antigens that are expressed intracellularly, e.g. structural or muscle proteins or transcription factors are analytical markers used to identify mesencephalic dopaminergic progenitor cells and/or subpopulations thereof, but cannot be used for enrichment of viable cells.

The term "expression" as used herein is defined as the transcription and/or translation of a particular nucleotide sequence driven by its promoter in a cell. The term "robust expression" as used herein refers to strong correlation of an antigen with a cellular phenotype (e.g. CD47 with FOXA2+ mesencephalic dopaminergic progenitor cells) and concomitant a sufficient strong expression of the same antigen allowing the implementation of an automated process for generation and separation of the cells expressing said antigen.

The term "sufficient strong expression" as used herein refers to the minimal or higher expression level of an antigen on a given cell allowing its isolation by either magnetic cell separation or fluorescent activated cell sorting.

The term "generating" in the context of generation of a cell population of mesencephalic dopaminergic progenitor cells by the method of the present invention has the same meaning as the term "producing" or "manufacturing". These terms describe the fact that at least a part of the cells of a starting cell composition are transformed to the target cells, i.e. mesencephalic dopaminergic progenitor cells, which then are isolated from non-target cells as disclosed by the method of the present invention.

The terms "method for a reproducible generation of a cell population of mesencephalic dopaminergic progenitor cells" or "method for a standardized generation of a population of mesencephalic dopaminergic progenitor cells" as used herein refer to a stable, reliable method resulting continuously in the same or at least very similar cell composition if comparable starting cell compositions are used. The variation of the results of the method, i.e. the cell composition, is minimal if the method is applied repeatedly. The influence of external parameters such as the capability of an operator becomes less important in a reproducible, standardized method, especially if the method is performed automatically in a closed cell sample processing system as disclosed herein. An important influence of the stability of the method as disclosed herein has the use of a robustly expressed cell surface marker, i.e. CD47, for separation of the target cells.

The term "target cells" as used herein refers to the cells which are the desired cells generated by the present invention. Regularly, the target cells are the CD47 positive mesencephalic dopaminergic progenitor cells. The cells which are not target cells are non-target cell, i.e. non-mesencephalic dopaminergic progenitor cells, these cells are also termed "other cells" to distinguish them from the mesencephalic dopaminergic progenitor cells.

The term "depletion" as used herein refers to a process of a negative selection that separates desired mesencephalic dopaminergic progenitor cells from undesired non-mesencephalic dopaminergic progenitor cells, i.e. the non-mesencephalic dopaminergic progenitor cells are removed from the sample. Regularly, the depletion is performed by a cell separation procedure such as magnetic cell sorting or fluorescent-activated cell sorting.

The term "tag" as used herein refers to the coupling of the antigen-binding molecule, e.g. an antibody or fragment thereof, to other molecules, e.g. particles, fluorophores, haptens like biotin, or larger surfaces such as culture dishes and microtiter plates. In some cases the coupling results in direct immobilization of the antigen-binding molecule, e.g. if the antigen-binding molecule is coupled to a larger surface of a culture dish. In other cases this coupling results in indirect immobilization, e.g. an antigen-binding molecule coupled directly or indirectly (via e.g. biotin) to a magnetic bead is immobilized if said bead is retained in a magnetic field. In further cases the coupling of the antigen-binding molecule to other molecules results not in a direct or indirect immobilization but allows for enrichment, separation, isolation, and detection of cells according to the present invention, e.g. if the antigen-binding molecule is coupled to a fluorophore which then allows discrimination of stronger labeled cells, weaker labeled cells, and non-labeled cells, e.g. via flow cytometry methods, like FACSorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "antigen-binding molecule" as used herein refers to any molecule that binds preferably to or is specific for the desired target molecule of the cell, i.e. the antigen. The term "antigen-binding molecule" comprises e.g. an antibody or antibody fragment. The term "antibody" as used herein refers to polyclonal or monoclonal antibodies, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "antibody" comprises both intact molecules and antibody fragments, such as Fab, Fab', F(ab')2, Fv and single-chain antibodies. Additionally, the term "antigen-binding molecule" includes any molecule other than antibodies or antibody fragments that binds preferentially to the desired target molecule of the cell. Suitable molecules include, without limitation, oligonucleotides known as aptamers that bind to desired target molecules, carbohydrates, lectins or any other antigen binding protein (e.g. receptor-ligand interaction). The linkage (coupling) between antibody and tag or particle can be covalent or non-covalent. A covalent linkage can be, e.g. the linkage to carboxyl-groups on polystyrene beads, or to NH2 or SH2 groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

The terms "specifically binds to" or "specific for" with respect to an antigen-binding molecule, e.g. an antibody or fragment thereof, refer to an antigen-binding molecule (in case of an antibody or fragment thereof to an antigen-binding domain) which recognizes and binds to a specific antigen in a sample, e.g. in the present invention CD47, but does not substantially recognize or bind other antigens in said sample. An antigen-binding domain of an antibody or fragment thereof that binds specifically to an antigen from one species may bind also to that antigen from another species. This cross-species reactivity is not contrary to the definition of "specific for" as used herein. An antigen-binding domain of an antibody or fragment thereof that specifically binds to an antigen, e.g. the CD47 antigen, may also bind substantially to different variants of said antigen (allelic variants, splice variants, isoforms etc.). This cross reactivity is not contrary to the definition of that antigen-binding domain as specific for the antigen, e.g. for CD47.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

For removal, enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells.

An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting mesencephalic floor plate (like) cells from a starting cell composition comprising pluripotent and/or multipotent stem cells according to the present invention monoclonal antibodies are used in conjunction with colloidal superparamagnetic microparticles having an organic coating by e.g. polysaccharides (Magnetic-activated cell sorting (MACS®) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads. The MACS® technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s). In case of a positive selection the cells expressing the antigen(s) of interest, which attached to the magnetic column, are washed out to a separate vessel, after removing the column from the magnetic field. In case of a negative selection the antibody used is directed against surface antigen(s), which are known to be present on cells that are not of interest. After application of the cells/magnetic nanoparticles solution onto the column the cells expressing these antigens bind to the column and the fraction that goes through is collected, as it contains the cells of interest. As these cells are non-labeled by an antibody coupled to nanoparticles, they are "untouched". The procedure can be performed using direct magnetic labeling or indirect magnetic labeling. For direct labeling the specific antibody is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads, anti-biotin MicroBeads, or anti-fluorophore MicroBeads. The above-described processes can also be performed in a closed cell sample processing system such as CliniMACS® (Miltenyi Biotec GmbH, Germany) or CliniMACS® Prodigy (Miltenyi Biotec GmbH, Germany).

The term "substantially pure cell composition of mesencephalic dopaminergic progenitor cells" as used herein refers to a cell composition comprising at least 70%, more preferentially at least 90%, most preferentially at least 95% of CD47 expressing mesencephalic progenitor cells co-expressing FOXA2 in final the cell composition obtained by the method of the present invention.

The mesencephalic dopaminergic progenitor cells obtainable by the methods disclosed herein may be used for subsequent steps such as research, diagnostics, pharmacological or clinical applications known to the person skilled in the art. Purification of mesencephalic dopaminergic progenitor cells from the variety of other cell types in the original tissue (e.g. adult brain, fetal cells) as well as in pluripotent stem cell differentiation cultures is a prerequisite for molecular, biochemical or electrophysiological in vitro analysis.

The enriched mesencephalic dopaminergic progenitor cells can also be used as a pharmaceutical composition in the therapy, e.g. cellular therapy, or prevention of diseases. The pharmaceutical composition may be transplanted into an animal or human, preferentially a human patient. The pharmaceutical composition can be used for the treatment and/or prevention of diseases in mammals, especially humans, possibly including administration of a pharmaceutically effective amount of the pharmaceutical composition to the mammal. The disease may be any disease, which can be treated and/or prevented through the presence of mesencephalic dopaminergic progenitor cells and/or through increasing the concentration of the relevant cells in/at the relevant place, e.g. in the place of the lost tissue of a patient suffering from Parkinson's disease. The treated and/or preventively treated disease may be any disease, which displays symptoms caused by the loss of dopamine neurons in a patient. The treatment may be the transplantation of enriched mesencephalic dopaminergic progenitor cells to the relevant place of the brain of the patient. Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The composition of mesencephalic dopaminergic progenitor cells obtained by the method of the present invention may be administered either alone, or as a pharmaceutical composition in combination with diluents and/or with other components such as cytokines or cell populations. Briefly, pharmaceutical compositions of the present invention may comprise the mesencephalic dopaminergic progenitor cells of the present invention as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The term "closed cell sample processing system" as used herein refers to any closed system which reduces the risk of cell culture contamination while performing culturing processes such as the introduction of new material and performing cell culturing steps such as proliferation, differentiation, activation, and/or separation of cells. Such a system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed cell sample processing system. This system is disclosed in WO2009/072003. But it is not intended to restrict the use of the method of the present invention to the CliniMACS® Prodigy.

The terms "automated method" or "automated process" as used herein refer to any process being automated through the use of devices and/or computers and computer softwares which otherwise would or could be performed manually by an operator. Methods (processes) that have been automated require less human intervention and less human time to deliver. In some instances the method of the present invention is automated if at least one step of the present method is performed without any human support or intervention. Preferentially the method of the present invention is automated if all steps of the method as disclosed herein are performed without human support or intervention. Preferentially the automated process is implemented on a closed cell sample processing system such as CliniMACS® Prodigy as disclosed herein.

The term "therapeutic effective amount" means an amount which provides a therapeutic benefit in a patient.

EXAMPLES

Example 1: Identification of CD47 on Mesencephalic Dopaminergic Progenitor Cells Human iPS cells were differentiated towards dopaminergic progenitors cells. The protocol was adapted from Kirkeby et al. 2012. For differentiation the iPS cells were harvested with TrypLE (Life Technologies, 12563-029). The cells from feeder co-cultivation underwent a feeder removal step (Miltenyi Biotec 130-095-531). Single cells were seeded in low attachment plates ($2\times10^6$/2 ml/6 well) to form EBs in DMEM-F12:MACS Neuro (1:1), N2 supplement (1:100; Gibco 17502-48), NeuroBrew-21 w/o vitamin A (1:50; Miltenyi Biotec 130-097-263), ROCK-Inhibitor (Thiazovivin 2 µM, Miltenyi Biotec 130-104-461 or Stemgent 04-0017) was added for the first two days. On d4, the cells were plated on polyornithine (PO: 15 µg/ml; Sigma P3655), fibronectin (FN: 5 µg/ml; BIOPUR AG 11-50-1104) and laminin (LN: 5 µg/ml; Sigma L20-20) coated plastic ware. From d0 to d9 the following neuralization and patterning factors were present SB431542 (10 µM, Stemgent 04-0010 or Miltenyi Biotec 130-105-336), LDN193189 (100 nM, Stemgent 04-0074 or Miltenyi Biotec 130-103-925), CHIR99021 (0.8 µM, Stemgent 04-0004 or Miltenyi Biotec 130-103-926), hSHH-C24-II (200 ng/ml, Miltenyi Biotec 130-095-727). From d2-d9 Purmorphamine (0.5 µM, Stemgent 04-0009 or Miltenyi Biotec 130-104-465) was added to the medium. On day 11 of differentiation, the cells were dissociated into single cells with accumax (eBioscience) and either used for an experiment or replated on dry PO/LN/FN coated plates in droplets of 10,000 cells/µl in MACS Neuro medium, NeuroBrew-21 w/o vitamin A (1:50), BDNF (20 ng/ml; Miltenyi Biotec 130-096-285), GDNF (10 ng/ml; Miltenyi Biotec 130-096-290) and ascorbic acid (200 µM; Sigma A5960). Either cells were used for sorting on day 16 or further differentiated beyond day 16. In the latter case, from d14 onwards, db-cAMP (0.5 µM; Sigma D0627) and/or DAPT (2.5 µM; Stemgent 04-0041) was added to the media for terminal differentiation.

A surface marker screen with 324 antibodies was conducted on mesencephalic floor plate cells at d11 of differentiation. Herein we used FOXA2 (BD, 561589) as counterstaining to identify the cells of interest. The marker was selected due to the co-expression with FOXA2. The best correlation was found with CD47 and FOXA2 (FIG. 5A, B). The same screen was also performed on d16 of differentiation and the correlation of CD47 and FOXA2 was still given.

Example 2: Verification of CD47 as a Marker for Mesencephalic Dopaminergic Progenitor Cells Derived from Different Pluripotent Stem Cell Sources To verify that CD47 is a marker for mesencephalic dopaminergic progenitor cells independent from the sources of PSCs used, we analysed the correlation of CD47 and FOXA2. We could show this correlation for the ES line (SA001) and two iPS lines (K10, viPS).

To further test the robustness of the marker, PSCs were cultivated either in feeder co-cultivation or feeder free (MG, VTN) cultivation systems prior to the differentiation.

The differentiation was started in low attachment plates or bacterial dishes (6 well, 12 well, 24 well, 6 cm dishes). As differentiation medium either MACS Neuro or Neurobasal has been used.

Example 3: Sorting Strategy of CD47 Positive Cells by Magnetic Cell Separation

CD47 was used to sort the FOXA2 positive cells out of a heterogenous midbrain dopaminergic differentiation culture either on d11 or d16.

The differentiated cells were harvested with accumax (eBioscience 00-4666-56) or accutase (Stemgent 01-0006). Separation was performed via an indirect magnetic labeling strategy (Miltenyi Biotec). In brief, $5\times10^6$ single cells were stained in 0.1 ml with primary antibody (CD47-PE Miltenyi Biotec; 130-101-350; positive enrichment: Titer 1:30 or negative fraction: Titer 1:10, Miltenyi Biotec) for 10 min at 4° C. Cells were washed with 2 ml medium, centrifuged and afterwards incubated for 15 min at 4° C. in 0.1 ml of a 1:5 dilution of anti-PE-MicroBeads in medium (Miltenyi Biotec; 130-048-801). Cells were washed with medium, centrifuged and resuspended in 0.5 ml medium. MS columns were equilibrated and placed in the magnet. Labeled cells were applied to the column and washed three times with medium by gravity flow. The flow through was collected as negative fraction. The positive fraction was eluted in 1 ml using the provided plunger. In order to achieve a higher purity a second MS column was used (FIG. 6).

The positive fraction was enriched of FOXA2/LMX1A cells (FIG. 7).

Example 4: Analyses of the CD47 Positive Cells

Figure 8:
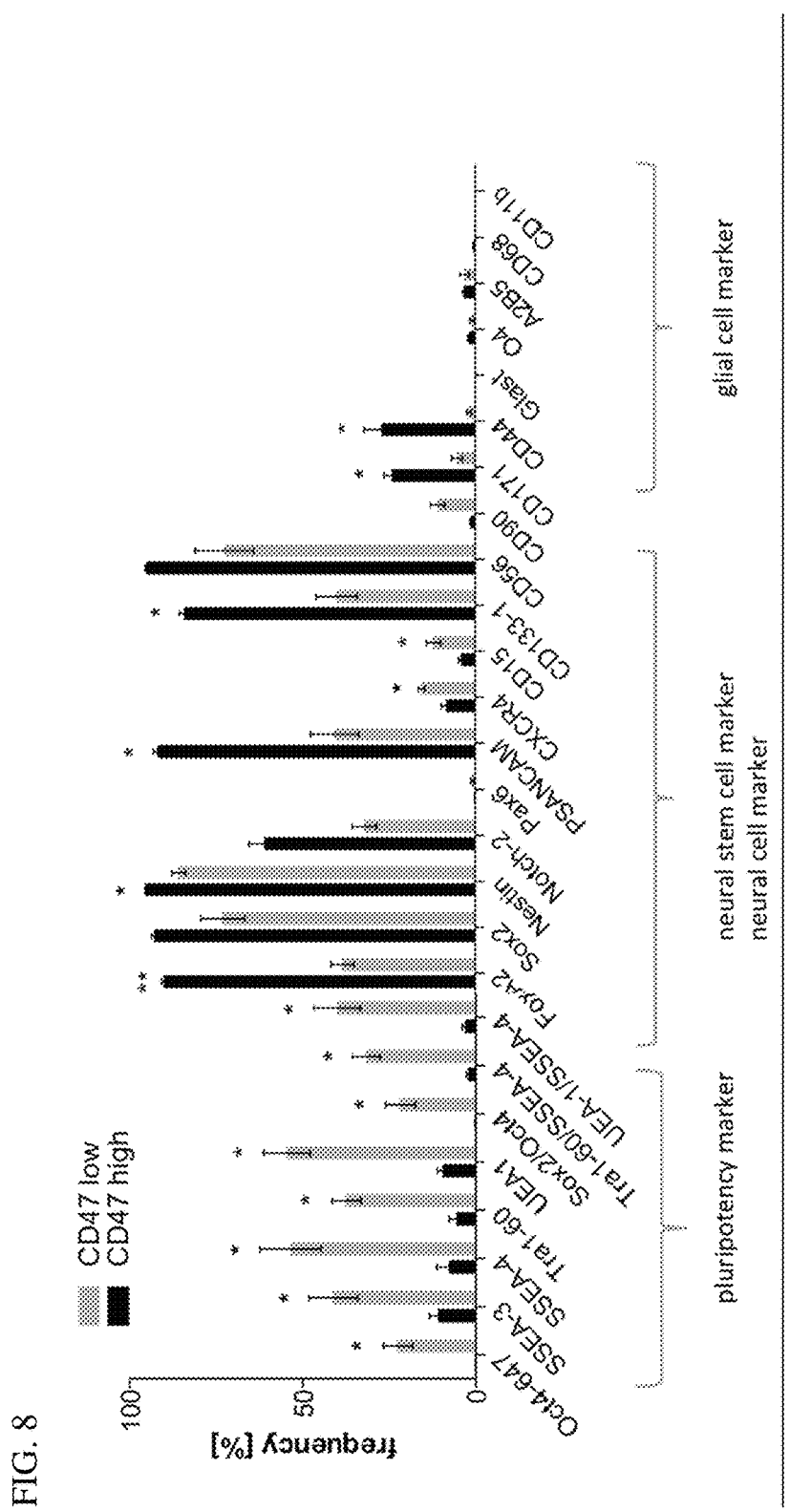
FIG. 8 shows flow cytometric characterization of CD47 expression in MDAPCs by co-staining of CD47 and markers specific for different neural subpopulations and pluripotency marker.

In order to define the CD47 low and high population in more detail, further analyses were performed. The CD47 positive fraction was almost absent of pluripotency marker compared to the CD47 low fraction (FIG. 8). Furthermore marker of the glial lineage like Glast, O4, A2B5 and CD11b were not expressed within the cell composition at day 11 of differentiation, which shows the specificity of the differentiation protocol towards mesencephalic floor plate cells. Neural cell and neural stem cell markers were expressed in both fractions but to a higher extend in the CD47 high expressing cells. This data shows that enrichment of CD47 leads to a homogenous culture without remaining pluripotent cells.

Example 5: Automated Differentiation of and Isolation of MDAPCs Using the ClinMACS Prodigy Device The automation of the differentiation and isolation of MDAPCs based on CD47 expression was implemented as follows. All cultivation steps were performed in the CliniMACS Prodigy tubing set TS730 (FIG. 1), modified by connecting tube extensions, accessories containing cell sampling pouches as well as Advanced cell culture bag (ACCB, Miltenyi Biotec, prototypes). First, a highly gas permeable ACCB containing 5 layers of polystyrol cultivation surface (total 500 $cm^2$) was sterilely connected to the tube behind valve 22 using a 1 meter tube extension (Miltenyi Biotec, 130-017-904).

After priming of the tubing step, i.e. conditioning, using rinsing buffer, a vitronectin solution (500 µg/ml) was transferred into said ACCB and incubated for 2 hours at RT. After coating, the vitronectin solution was removed and $7.5 \times 10^6$ iPS cells were suspended in 75 ml StemMACS™ iPS-Brew XF Media (MiltenyiBiotec), supplemented with 2 µM Thiazovivin, and sterilely transferred into a Cell transfer bag, divided by a bag clamp and another 75 ml StemMACS™ iPS-Brew XF Media (MiltenyiBiotec) supplemented with 2 µM Thiazovivin was filled into the bag above the bag clamp. The bag was sterilely connected to TS730 and the cell suspension was transferred into the ACCB. After that, the bag clamp was opened to flush out and transfer remaining cells out of the cell transfer bag into the connected ACCB behind valve 22. The ACCB was placed into an adjacent gas and heat controlled cell culture incubator. Automated media exchange was conducted at day 2 (full media change) and day 3-5 (70% media exchange using) using StemMACS™ iPS-Brew XF Media without addition of Thizovivin. At day 4 of iPSC expansion, the CCU was prepared for the EB generation step, by coating with a PHEMA solution. Therefore, between two media changes 40 ml of a 20 mg/ml PHEMA (Sigma; Cat. #P3932) in 95% ethanol was transferred into the CCU and the incubation chamber was heated to 37° C. over night, to allow evaporation of ethanol and deposition of the polymer preventing later cell attachment. The chamber was washed twice using buffer. At day 5 of iPS culture, iPSC were harvested form the ACCB, by first washing with media, incubation with TrypLE (Life Technologies; #12563-029) for 7 min, followed by enzyme inhibition using 0.5 mg/ml soybean inhibitor (Soybean Trypsin-Inhibitor; Life Technologies; #17075029) in PBS. Cells were transferred into the CCU, a sample was transferred into a sampling pouch as part of a connected accessory tube (Triple Sampling Adapter, Miltenyi Biotec 130-017-907) behind valve 20 (connected using a three-way stop cock behind valve 20) to assess cell concentration. $120 \times 10^6$ cells were harvested and washed 3 times, i.e. sedimented by horizontal centrifugation and resuspended in media, using the centrifugation unit (CCU) and resuspended in 120 ml ($1 \times 10^6$/ml) differentiation media. 20 ml of cell suspension was discarded (pumped into bag 5) to adjust to 100 ml of suspension culture volume within the CCU. The CCU was incubated at 37° C. headspace gas was adjusted to 5% CO2. As differentiation media DMEM-F12:MACS Neuro (1:1), N2 supplement (1:100; Gibco 17502-48), NeuroBrew-21 w/o vitamin A (1:50; Miltenyi Biotec 130-097-263), ROCK-Inhibitor (Thiazovivin 2 µM, Miltenyi Biotec 130-104-461 or Stemgent 04-0017) was added for the first two days to allow efficient formation of embryoid bodies (EBs, EB-differentiation step), i.e. spheroid cell clusters or aggregates. From d0 to d9 the following neuralization and patterning factors were present SB431542 (10 µM, Stemgent 04-0010 or Miltenyi Biotec 130-105-336), LDN193189 (100 nM, Stemgent 04-0074 or Miltenyi Biotec 130-103-925), CHIR99021 (0.8 µM, Stemgent 04-0004 or Miltenyi Biotec 130-103-926), hSHH-C24-II (200 ng/ml, Miltenyi Biotec 130-095-727). From d2-d9 Purmorphamine (0.5 µM, Stemgent 04-0009 or Miltenyi Biotec 130-104-465) was added to the medium. 6 h after EB generation, the CCU was set to shaking mode, i.e. 300 rpm rotation in one direction for 2 sec, followed by 300 rpm rotation in opposite direction, followed by 30 sec without rotation, ensuring aeration of the cell culture medium. At day two of the EB-differentiation step a new ACCB with a total of cultivation area of 300 cm² was sterilely connected to the tube controlled by valve 21 using a 1 meter tube extension and subsequently coated with a mix of PO, fibronectin (FN) and laminin (LN) (PO: 15 µg/ml, Sigma P3655; FN: 5 µg/ml; BIOPUR AG 11-50-1104; LN: 5 µg/ml; Sigma L20-20) for two days at 37° C. (the bag placed into an adjacent cell culture incubator). On d4, coating solution was removed from the ACCB controlled by valve 21, rinsed with differentiation media before the EB suspension was transferred into the bag. For that purpose the EB suspension in the CCU was washed and resuspended in differentiation media (supplemented according to the above instructions for day 4) and transferred into the prepared ACCB controlled by valve 21 and incubated at 37° C. (the bag placed into an adjacent cell culture incubator). Media changes were conducted at days 2, 4, 6, 8, 9, the differentiation media supplemented according to the above instructions for the respective day of differentiation. On day 9 a new ACCB (surface area 200 cm²) was welded to the tube behind valve 22 replacing the initial culture bag for the iPS expansion step, and was coated coated with a mix of PO, fibronectin (FN) and laminin (LN) for 2 days at 37° C. (as before). On day 11 of differentiation, the cells were dissociated into single cells with accumax (eBioscience) and optionally passed through a tubing loop equipped with cell strainer units with decreasing pore size (FIG. 3), in this case 100, 100, 70, 30 µm), integrated between the CCU and valve 24 using 2 three-way stop cocks, thereby breaking down cell aggregates and or remove unwanted cell clusters. Cells were transferred into the CCU, a sample was transferred into a sampling pouch as part of a connected accessory tube behind valve 20 (connected using a three-way stop cock behind valve 20) to assess cell concentration. $225 \times 10^6$ cells were harvested and washed 3 times, i.e. sedimented by horizontal centrifugation and resuspended in media, using the centrifugation unit (CCU) and resuspended in 100 ml ($2 \times 10^6$/ml; $200 \times 10^6$/200 cm²) differentiation media, i.e. MACS Neuro medium, NeuroBrew-21 w/o vitamin A (1:50), BDNF (20 ng/ml; Miltenyi Biotec 130-096-285), GDNF (10 ng/ml; Miltenyi Biotec 130-096-290) and ascorbic acid (200 µM; Sigma A5960). Cells were transferred to the bag welded to the tube behind valve 22 in MACS Neuro medium, Neuro-Brew-21 w/o vitamin A (1:50), BDNF (20 ng/ml; Miltenyi Biotec 130-096-285), GDNF (10 ng/ml; Miltenyi Biotec 130-096-290) and ascorbic acid (200 µM; Sigma A5960). A media change was conducted at day 13 and 15.

On day 16 of differentiation, the cells were dissociated into single cells with accumax (eBioscience) and optionally passed through a tubing loop equipped with cell strainer units with decreasing pore size (in this case 100, 100, 70, 30 µm), integrated between the CCU and valve 24 using 2 three-way stop cocks, thereby breaking down cell aggregates and or remove unwanted cell clusters. Cells were transferred into the CCU, a sample was transferred into a sampling pouch as part of a connected accessory tube behind valve 20 (connected using a three-way stop cock behind valve 20) to assess cell concentration. $225 \times 10^6$ cells were harvested and washed 3 times, i.e. sedimented bei horizontal centrifugation and resuspended in media, using the centrifugation unit (CCU) and resuspended in 10 ml ($22.5 \times 10^6$/ml) buffer (CliniMACS® PBS/EDTA+0.5% HSA) and transferred to a cell transfer bag connected to valve 10 and welded off the TS. A new TS510 (FIG. 2) was subsequently installed, primed (i.e. equilbrated using CliniMACS® PBS/EDTA+0.5% HSA, the cell bag connected to the TS and cellsuspension was transeferred to the CCU. Additionally, 500 µl of CD47-PE (Miltenyi Biotec; 130-101-350) mixed with 4.5 ml CliniMACS® PBS/EDTA+0.5% HSA in a CryoMACS freezing bag (Miltenyi-Biotec 200-074-400) was sterilely connected to the TS at valve 2 and transferred into the CCU (primary labeling). Cells were incubated at 4° C. for 15 min, then washed with CliniMACS® PBS/EDTA+ 0.5% HSA sedimented and resuspended in 20 ml CliniMACS® PBS/EDTA+0.5% HSA. Thereafter, secondary labeling was conducted by transferring 2.27 ml Anti-PE MicroBeads (Miltenyi Biotec; 130-048-801) mixed with 2.73 ml CliniMACS® PBS/EDTA+0.5% HSA from a CryoMACS freezing bag (Miltenyi-Biotec 200-074-400) sterilely connected to the TS at valve 3 to the CCU. Cells were incubated at 4° C. for 10 min, then washed with CliniMACS® PBS/EDTA+0.5% HSA sedimented and resuspended in 20 ml CliniMACS® PBS/EDTA+0.5% HSA and applied to the preequilibrated separation column. After column wash cells were eluted from the column and transferred to the Target Cell bag. Using this process a cell composition of $1 \times 10^7$ MDAPCs could be retrieved at a purity of 95%.

What is claimed is:

1. A method for generating a cell composition of mesencephalic dopaminergic progenitor cells from a starting cell composition comprising pluripotent and/or multipotent stem cells, the method comprising the steps of
   a) differentiating said pluripotent and/or multipotent stem cells into mesencephalic dopaminergic progenitor cells, thereby generating a cell population comprising mesencephalic dopaminergic progenitor cells and other cells,
   b) dissociating the differentiated cells of step a) into a single cell suspension,
   c) enriching said mesencephalic dopaminergic progenitor cells by using an antigen binding molecule specific for the CD47 antigen for positive selection of said mesencephalic dopaminergic progenitor cells in said single cell suspension.

2. The method according to claim 1, wherein said pluripotent and/or multipotent stem cells are proliferated in a proliferation step before step a).

3. The method according to claim 1, wherein said method is performed in a closed cell sample processing system.

4. The method according to claim 3, wherein said method is an automated method.

5. The method according to claim 1, wherein said antigen binding molecule specific for the CD47 antigen is an anti-CD47 antibody or antigen binding fragment thereof.

6. The method according to claim 1, wherein the step of enrichment of said mesencephalic dopaminergic progenitor cells is performed by fluorescent activated cell sorting or magnetic cell sorting.

7. The method of claim 1, wherein the mesencephalic dopaminergic progenitor cells are human or non-human primate cells.

* * * * *